United States Patent [19]

Omura et al.

[11] Patent Number: 5,042,304
[45] Date of Patent: Aug. 27, 1991

[54] ULTRASONIC MICROSCOPE

[75] Inventors: Yasuhiro Omura; Yasuo Sasaki; Mitsugu Sakai, all of Hachioji; Koichi Karaki, Hino, all of Japan

[73] Assignee: Olympus Optical Co., Ltd., Tokyo, Japan

[21] Appl. No.: 460,277

[22] Filed: Jan. 2, 1990

[30] Foreign Application Priority Data

Jan. 19, 1989 [JP] Japan ................... 1-3878[U]

[51] Int. Cl.$^5$ ........................................... G01N 29/00
[52] U.S. Cl. ................................................. 73/606
[58] Field of Search ............... 73/620, 644, 606, 607, 73/866.1, 866.5, 863.25

[56] References Cited

U.S. PATENT DOCUMENTS

| 4,543,838 | 10/1985 | Fohler | 73/866.5 |
| 4,742,717 | 5/1988 | Ichino | 73/866.5 |
| 4,920,803 | 5/1990 | Karaki et al. | 73/606 |

FOREIGN PATENT DOCUMENTS

3924006A1  1/1990  Fed. Rep. of Germany .

OTHER PUBLICATIONS

Acoustical Imaging, vol. 12, pp. 17–18, Plenum Press, (date unknown).
"The Journal of Acoustic Society of America"; Cryogenic Acoustic Microscopy: J. Heiserman et al, 67(5), May 1980, pp. 1629–1637.

Primary Examiner—Hezron E. Williams
Assistant Examiner—Louis M. Arana
Attorney, Agent, or Firm—Frishauf, Holtz, Goodman & Woodward

[57] ABSTRACT

An ultrasonic microscope includes a container for containing a liquid nitrogen, and an acoustic lens housed in the container to emit an ultrasonic beam onto the view face of a sample. A sleeve is located above the container, which has a gas-tight chamber therein communicated with the container and a sample inserting opening formed in the periphery thereof. The sample inserting opening is selectively closed and opened by a gate valve. A sample rod is provided with a sample on its lower end, and may be freely movable up and down in the gas-tight chamber to a position where the sample in the container is scanned and to another position adjacent to the sample inserting opening where the sample is exchanged with a new one.

10 Claims, 7 Drawing Sheets

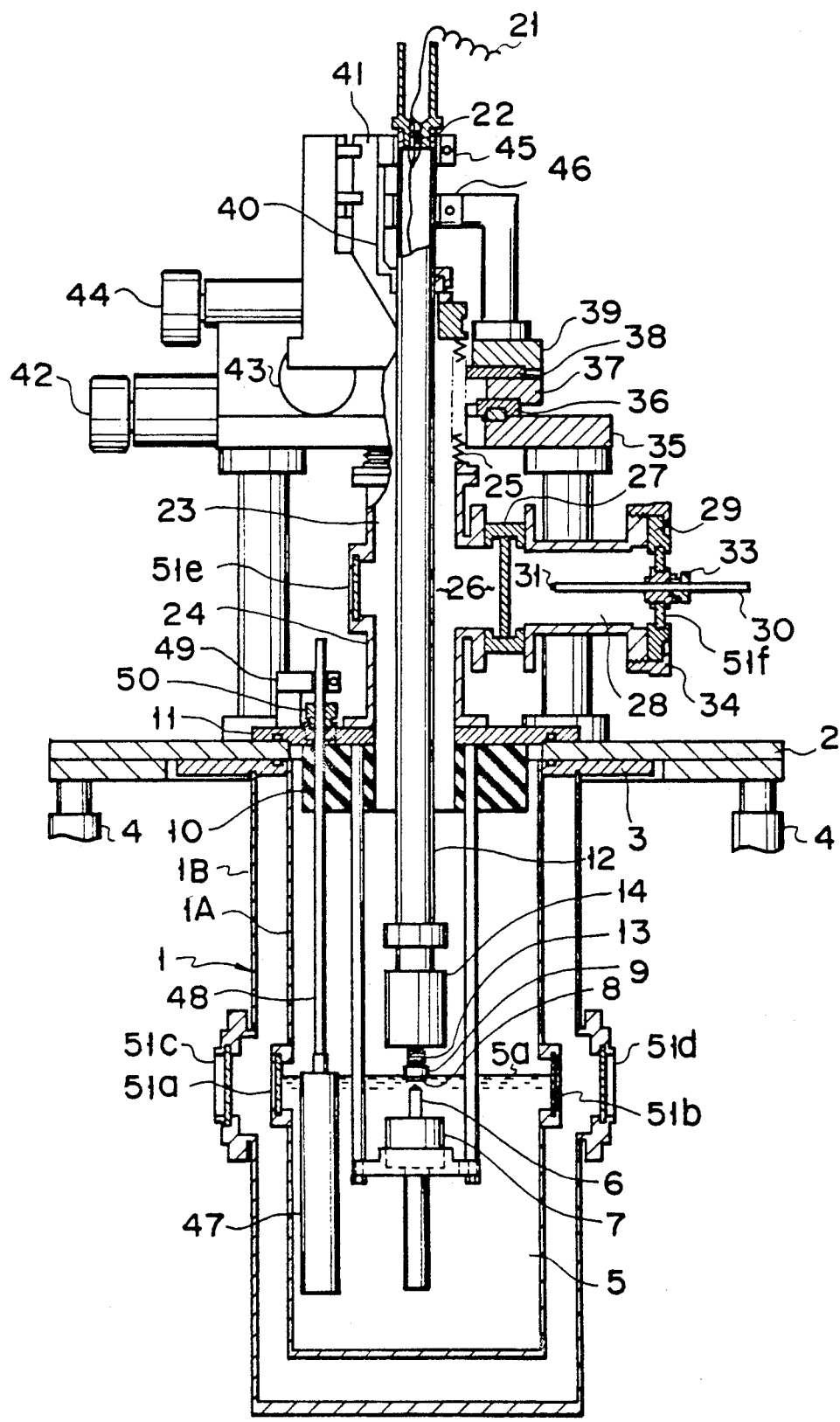
F I G. 1

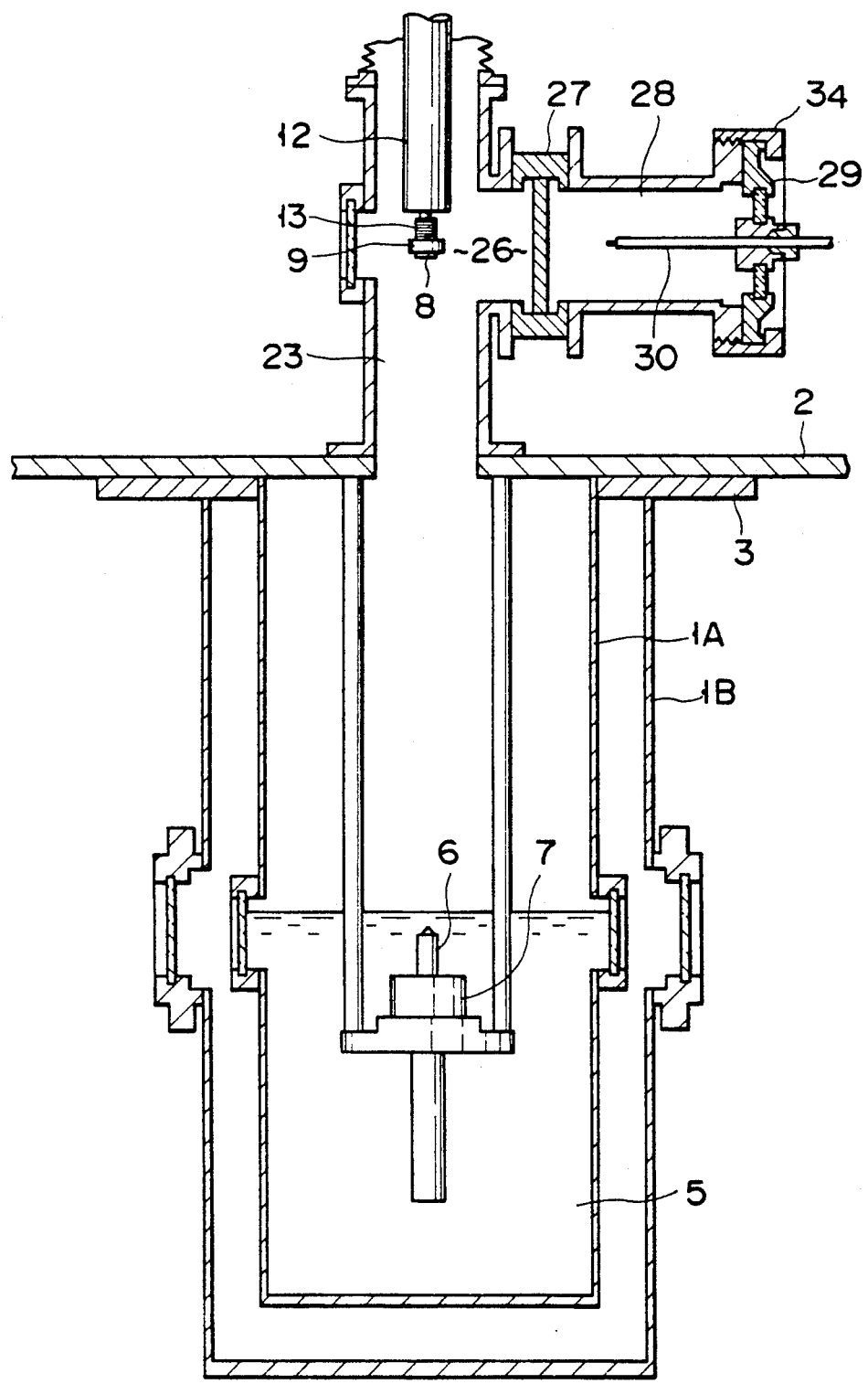
F I G. 5

ULTRASONIC MICROSCOPE

BACKGROUND OF THE INVENTION

1. Field of the Invention

The present invention relates to an ultrasonic microscope intended to scan that face of a sample which is to be viewed through the microscope with an ultrasonic beam and, more particularly, it relates to an ultrasonic microscope intended to use, as a coupler liquid, a low temperature liquid such as nitrogen, argon and helium liquids.

2. Description of the Related Art

The ultrasonic microscope which has been recently developed attracts attention these days as a third microscope following the optical and electronic ones. The ultrasonic microscope can obtain the image of a sample in such a way that an ultrasonic beam is focused onto the viewed face of the sample by means of an acoustic lens to two-dimensionally scan the face of the sample. When an ultrasonic wave of high frequencies (ranging from several hundreds MHz to several GHz) is used to increase resolving power in the case of this microscope, the interval between the acoustic lens and the sample must be made smaller as the frequency of the ultrasonic wave becomes higher because the acoustic absorption ratio of coupler liquid (or water) is proportional to the square of frequency. The interval between the acoustic lens and the sample is defined by the curvature radius of the acoustic lens. An acoustic lens having a small radius of curvature must be used to shorten the interval. In a case where the frequency of ultrasonic wave used is several GHz, for example, the curvature radius of acoustic lens must be made smaller than several tens μm. It is extremely difficult to make an acoustic lens which has such a finely curved surface. Even if such acoustic lens can be made, it will raise the cost of the microscope.

To enhance resolving power without setting the curvature radius of acoustic lens to the above-mentioned value, there has been provided another supersonic microscope (which will be hereinafter referred to as a low temperature ultrasonic microscope) intended to use, as coupler liquid, a low temperature liquid having a lower sound speed than that of water, such as nitrogen, argon and helium liquids and to scan the viewed face of sample in this low temperature liquid.

According to the low temperature ultrasonic microscope disclosed in U.S. Pat. No. 4,920,803 for example, however, the sample rod arranged freely movable up and down in the gas-tight chamber must be pulled completely out of the chamber in a case where the sample is to be exchanged with a new one. The sample rod is sealed by an O-ring and it must pass through the O-ring when it is to be pulled completely out of the gas-tight chamber. This makes it necessary for the sample rod to have a same radius all over its whole length. In other words, such a focusing system as disclosed in U.S. patent application Ser. No. 07/399,318 and having a radius larger than that of the sample rod could not be attached to the lower end of the sample rod.

SUMMARY OF THE INVENTION

The object of the present invention is to provide an ultrasonic microscope capable of carrying out sample exchange without pulling the sample rod completely out of the gas-tight chamber.

BRIEF DESCRIPTION OF THE DRAWINGS

FIGS. 1 through 11 show an example of the ultrasonic microscope according to the present invention, in which:

FIG. 1 is a vertically-sectioned view showing the ultrasonic microscope;

FIG. 2 shows a system for holding and drawing a sample holder;

FIG. 3 is a perspective view showing a system for positioning the sample holder;

FIG. 4 shows the front end of a sample inserting rod; and

FIGS. 5 through 11 show the process of exchanging the sample with a new one.

DETAILED DESCRIPTION OF THE PREFERRED EMBODIMENTS

Figure 2:
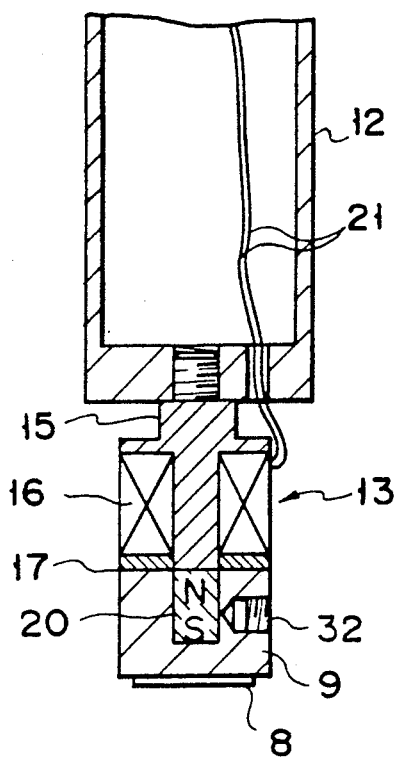

FIG. 1 is a vertically-sectioned view showing one embodiment of the ultrasonic microscope according to the present invention. Cylindrical heat-insulating container 1 having an opening on the top is air-tightly fixed to the underside of base plate 2, which also has an opening, through flange 3. Base plate 2 is horizontally supported on a support stand (not shown) by plural air dampers 4 which are connected to the underside of base plate 2. Heat-insulating container 1 is of the double type comprising inner and outer vessels 1A and 1B. The space between inner and outer vessels 1A and 1B is evacuated to prevent temperature outside the container 1 from being transmitted from outer vessel 1B to inner one 1A to heat coupler liquid in container 1.

Liquid nitrogen 5, which serves as a coupler liquid, and acoustic lens 6 are housed in inner vessel 1A. Acoustic lens 6 is supported on XY scanner 7 with its ultrasonic beam injector directed upward, and can be moved under this state in a plane X - Y perpendicular to the paper sheet on which FIG. 1 is drawn. Sample holder 9 holds sample 8 so that its measured surface is directed to the acoustic lens and located above acoustic lens 6. Ring-shaped heat insulator 10 is arranged in the opening at the top of inner vessel 1A to prevent heat from entering into container 1 through the opening. It is attached to the underside of lid 11 which closes the opening of base plate 2. Lid 11 is provided in the center thereof with a circular opening which corresponds to the opening of ring-shaped heat insulator 10 and through which inner vessel 1A is communicated with gas-tight chamber 23 which will be described later.

Sample holder 9 is attached to the lower end of sample rod 12, which extends vertically through gas-tight chamber 23 and enters into inner vessel 1A through openings of lid 11 and heat insulator 10. Sample holder 9 is made of non-magnetic material and sample rod 12 has at the lower end portion thereof system 13 for holding sample holder 9 drawn. Sample rod 12 also has focusing system 14 above system 13. Focusing system 14 is intended to adjust the focusing point of acoustic lens 6, driving sample holder 9 in direction Z (or vertical direction) by means of voice coils.

Figure 3:
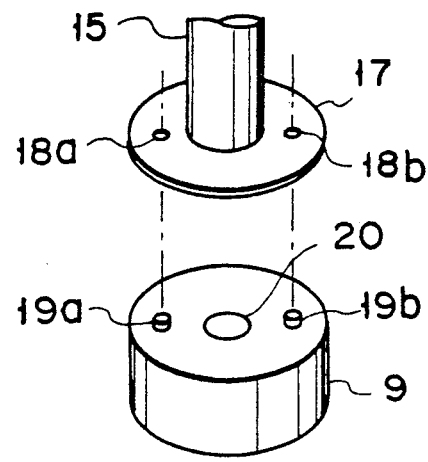

System 13 for drawing sample holder 9 includes core 15 made of magnetic material and screwed into the lower end of sample rod 12 at the top thereof, coil 16 wound round core 15, and ring-shaped outer lid 17 drawn onto the lower end of core 15 and made of non-magnetic material, as shown in FIG. 2 (in which focusing system 14 is not shown). When power is supplied to coil 16, a magnetic field is generated to draw and hold sample holder 9 to outer lid 17. As shown in FIG. 3, outer lid 17 has two positioning holes 18a and 18b separated from each other by a predetermined distance. Two positioning pins 19a and 19b are erected from the top of sample holder 9 to enter into their corresponding positioning holes 18a and 18b of outer lid 17. Permanent magnet 20 is embedded in sample holder 9, which can also be drawn to outer lid 17 due to the magnetic force of this permanent magnet 20. This is because liquid nitrogen 5 is boiled by the heating of coil 16 to make images blurred or doubled when excessive power is supplied to coil 16 in gas-tight chamber 23.

Sample rod 12 is made hollow and lead lines 21 through which power is supplied to systems 13 and 14 are introduced outside from these systems, passing through sample rod 12 and hermetic seal section 22 on the top of sample rod 12. Sample rod 12 can move up and down in gas-tight chamber 23 located above heat-insulating container 1. Gas-tight chamber 23 is defined by cylindrical sleeve 24 gas-tightly fixed onto the top of lid 11, bellows 25 located on the top of cylindrical sleeve 24, and the like. Cylindrical sleeve 24 is provided with sample inserting opening 26 at the peripheral wall thereof. A cylindrical body having vacuum dehydration chamber 28 therein is connected to the periphery of sample inserting opening 26 through gate valve 27. Gas-tight and vacuum dehydration chambers 23 and 28 are selectively communicated with and sealed from each other by gate valve 27. Window 51f is attached to the outer end of the cylindrical body, which has vacuum dehydration chamber 28 therein, through outer flange 29. As the result, vacuum dehydration chamber 28 can be kept gas-tight from outside. Sample inserting rod 30 is inserted into vacuum dehydration chamber 28 in a direction perpendicular to sample rod 12, passing through the central hole of viewing window 51f, and sample exchange can be carried out, as will be described below, using this sample inserting rod 30.

Figure 4:
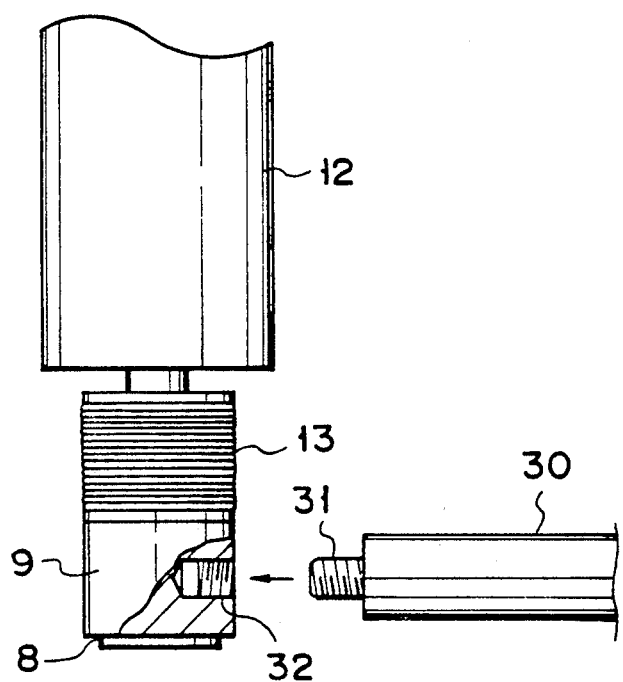

As shown in FIG. 4, threaded portion 31 is projected from the front end of sample inserting rod 30. When this threaded portion 31 is screwed into screw hole 32 in the peripheral wall of sample holder 9, sample holder 9 can be transferred by sample inserting rod 30. This sample inserting rod 30 is air-tightly passed through viewing window 51f by means of an O-ring and cap screw 33. Outer flange 29 can be detached from the opening of vacuum dehydration chamber 28 when clamp ring 34 which is screwed onto the outer end of the cylindrical body with outer flange 29 sandwiched is loosened.

Stage base 35 is located above base plate 2 and horizontally supported on plural pole braces, as shown in FIG. 1. Stage 37 for moving sample rod 12 in direction Y (or direction perpendicular to the paper sheet on which FIG. 1 is drawn) is mounted on stage base 35 through guide rail 36. Another stage 39 for moving sample rod in direction X (or right and left in FIG. 1) is mounted on stage 37 through guide rail 38. Further stage 41 for moving sample rod 12 in direction Z (or up and down in FIG. 1) is mounted on stage 39 through guide rail 40. These stages 37, 39 and 41 are driven by motors to move along their respective guide rails. Manual adjusting dial meters 42, 43 and 44 are attached to these motors, respectively. Stages 39 and 41 are provided with clamps 45 and 46 for clamping and fixing sample rod 12 and they move sample rod 12 through these clamps 45 and 46, while stage 37 moves it in direction Y through stage 39.

Float 47 for adjusting surface 5a of liquid nitrogen 5 at a certain level is housed in inner vessel 1A. Float 47 is formed of a cylinder made by a thin metal plate welded and it is provided with small holes at its top to prevent liquid nitrogen 5 in container 1 from being heated by gas in its hollow portion during the sample viewing process or to effectively cool its hollow portion by liquid nitrogen 5 before the sample viewing process. It is attached to the lower end of float support rod 48, which extends, freely movable in the vertical direction, through lid 11 and heat insulator 10 and enters into inner vessel 1A. Float support rod 48 is detachably clamped by clamp 49 which is erected from the top of base plate 2 and it can be fixed at any optional position where it is kept vertical. It is air-tightly passed through lid 11 by means of an O-ring and cap screw 50. Reference numerals 51a, 51b, 51c, 51d and 51e in FIG. 1 represent viewing windows similar to the one 51f.

Figure 6:
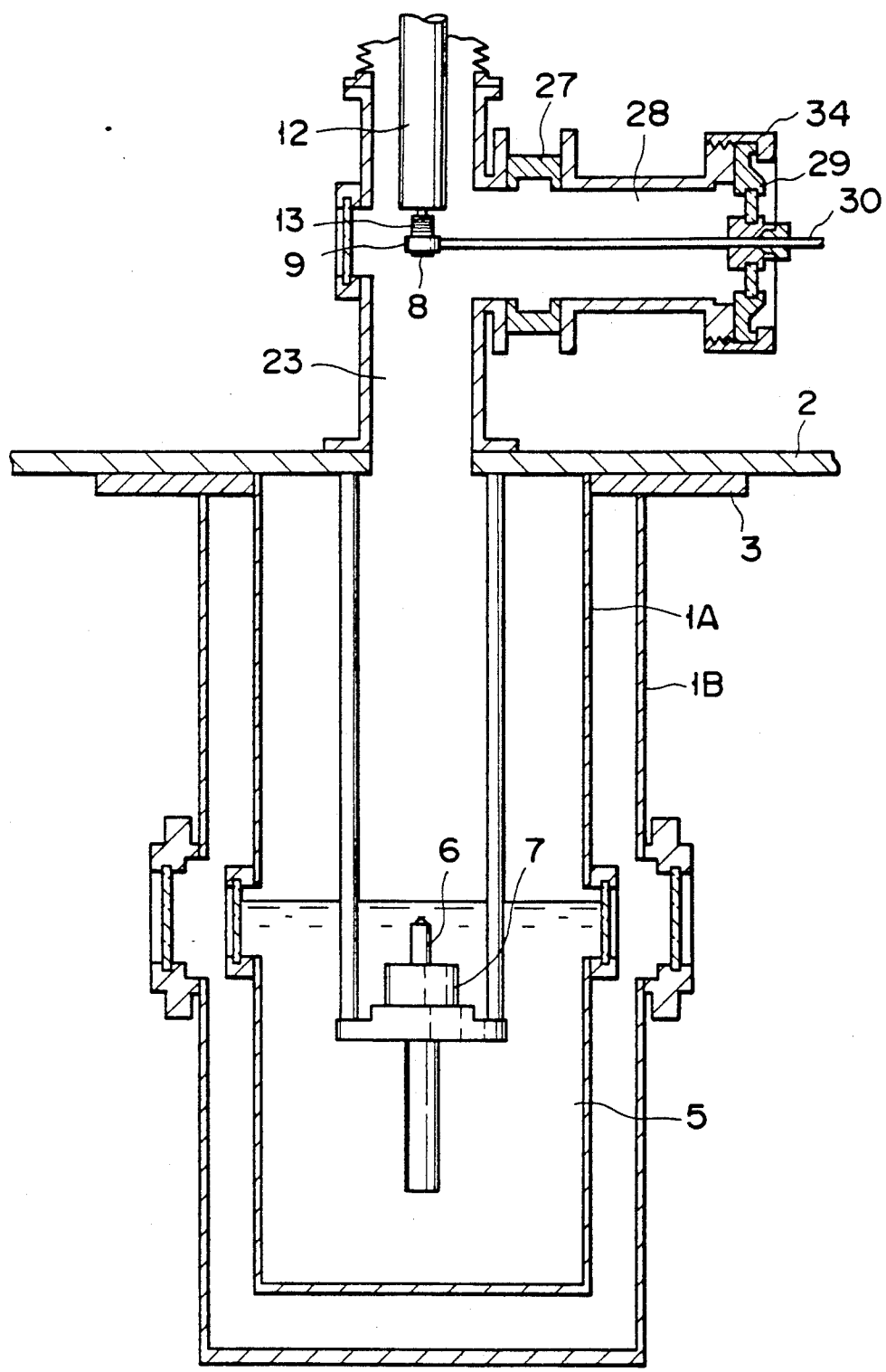
Figure 7:
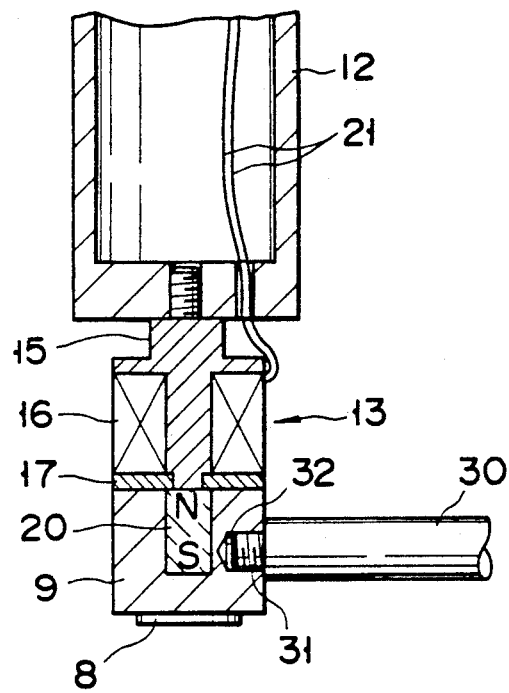
Figure 8:
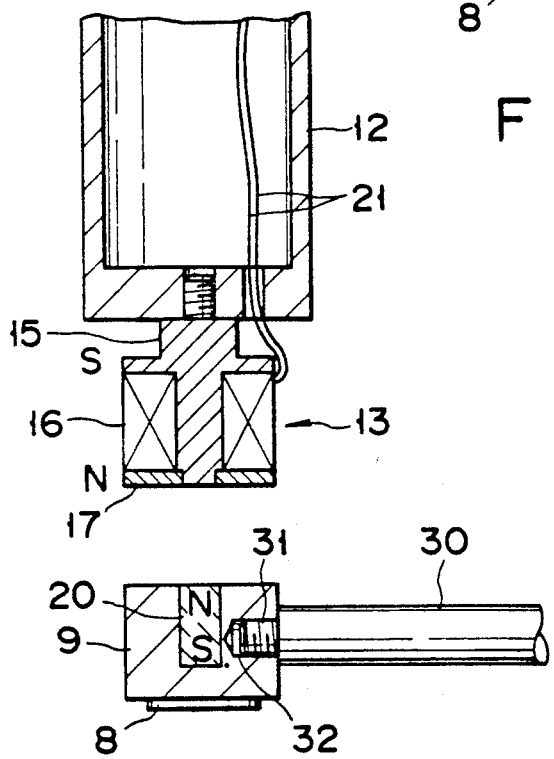
Figure 9:
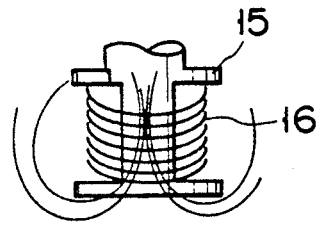

When sample 8 supported on the lower end of sample rod 12 is to be exchanged with a new one in the ultrasonic microscope having the above-described arrangement, sample rod 12 is pulled upward and its lower end is positioned, as shown in FIG. 5, to face sample inserting opening 26 which is formed on one side of gas-tight chamber 23. Gate valve 27 at sample inserting opening 26 is then opened and sample inserting rod 30 is inserted into gas-tight chamber 23, screwing threaded portion 31, which is projected from the front end of sample inserting rod 30, into screw hole 32 in the side of sample holder 9, as shown in FIGS. 6 and 7. The direction of current flowing through coil 16 for system 13 is changed over to separate sample holder 9 from the lower end of sample rod 12, as shown in FIG. 8, due to the repulsive force of permanent magnets embedded in core 15 and sample holder 9, respectively. In a case where outer lid 17 is made of magnetic material similarly to the case of core 15, magnetic flux generated at core 15 is roundly closed, as shown in FIG. 9, and the force of repulsing sample holder 9 against core 15 becomes weaker. When outer lid 17 is made of nonmagnetic material, therefore, larger repulsive force can be created with less power.

Figure 10:
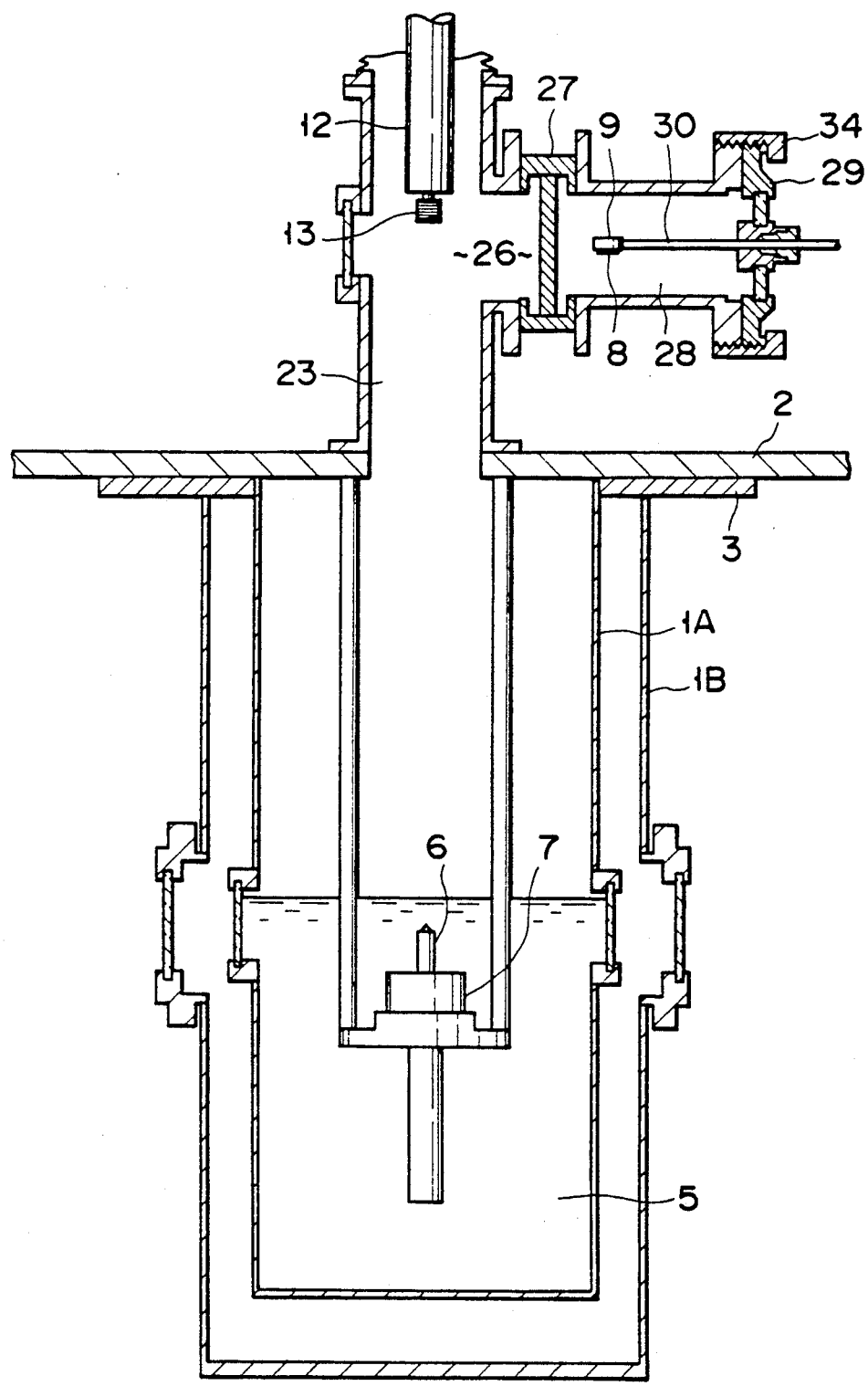
Figure 11:
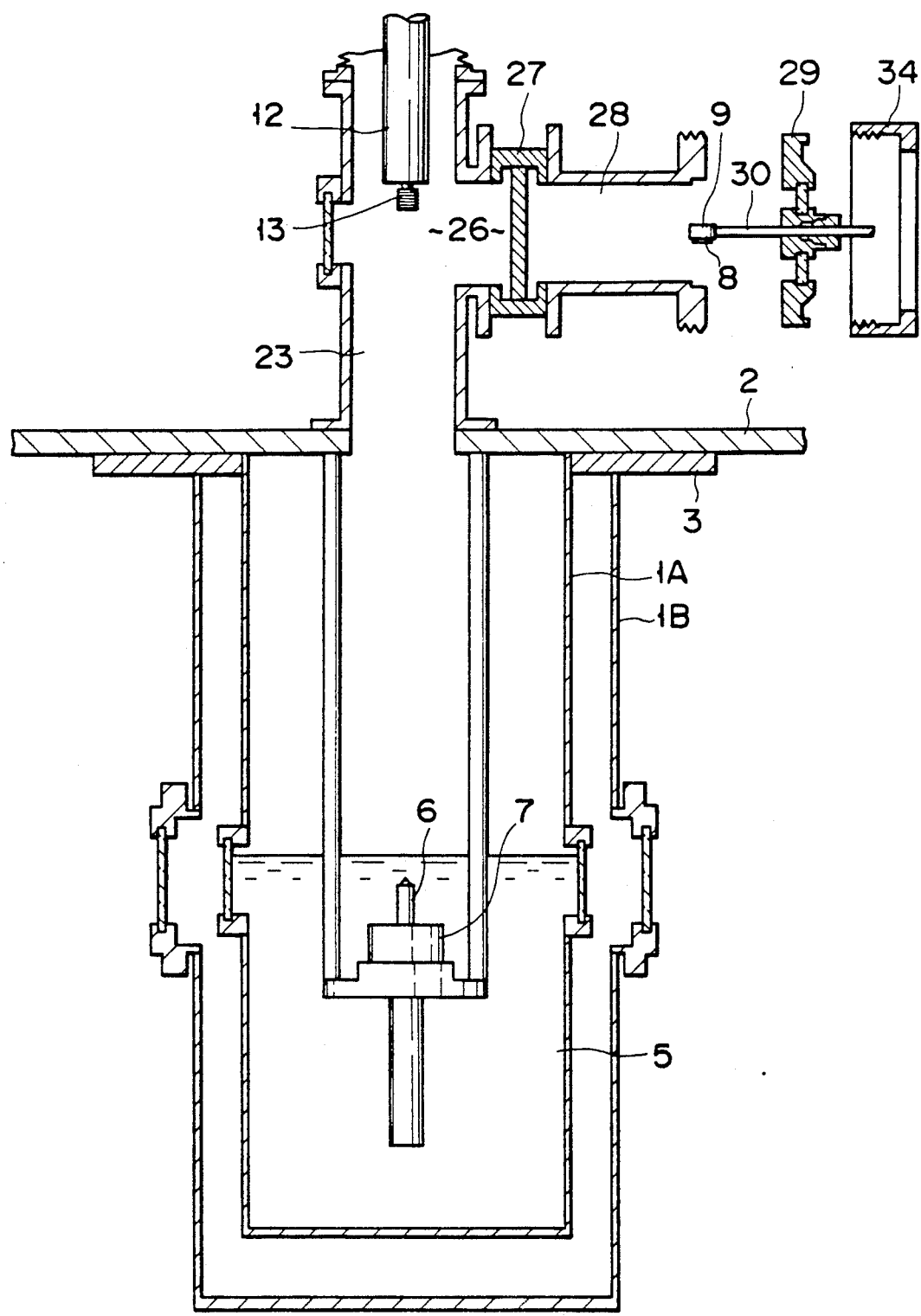

When sample holder 9 is separated from the lower end of sample rod 12 in this manner, sample inserting rod 30 is pulled back into vacuum dehydration chamber 28 and gate valve 27 is closed, as shown in FIG. 10. When vacuum dehydration chamber 28 is then evacuated by a vacuum pump and water is removed from sample holder 9, sample holder 9 is picked up from the front end of sample inserting rod 30 and out of vacuum dehydration chamber 28, while loosening cap ring 34 and detaching outer flange 29 from vacuum dehydration chamber 28, as shown in FIG. 11. When sample holder 9 is to be attached to the lower end of sample rod 12, the above-described process is reversed.

According to the ultrasonic microscope of the present invention as described above, sample inserting opening 26 provided with gate valve 27 is formed on one side of gas-tight chamber 23 and sample exchange is carried out through sample inserting opening 26. Therefore, sample exchange can be carried out without pulling sample rod 12 completely out of gas-tight chamber 23. This enables sample 8, focusing system 14 and the like each having a diameter larger than that of the sample rod to be attached to the lower end of sample rod 12.

Although sample exchange has been conducted, inserting sample inserting rod 30 into gas-tight chamber 23, in the above-described example, it is not limited to this manner. Although liquid nitrogen 5 has been used as a coupler liquid in the above case, low temperature liquid such as argon and helium liquids and water may be used instead.

As described above, the sample inserting opening provided with the gate valve is formed on one side of the gas-tight chamber and sample exchange is carried out through the sample inserting opening in the case of the present invention. This enables sample exchange to be conducted without pulling the sample rod completely out of the gas-tight chamber. Further, a sample, the focusing system and the like each having a diameter larger than that of the sample rod can be attached to the lower end of the sample rod.

What is claimed is:

1. An ultrasonic microscope, comprising:
   a container for containing a coupler liquid therein and having an opening at a top thereof;
   a sleeve located above the container and having a gas-tight chamber therein communicated with the container through the opening of the container and a sample inserting opening formed on one periphery thereof;
   a sample rod freely movable up and down in the gas-tight chamber and container between a first position where a sample in the container is scanned by scanner means and a second position adjacent to the sample inserting opening;
   means for holding the sample on the lower end of the sample rod;
   means housed in the container to face the sample and scan it with an ultrasonic beam;
   a gate valve for closing and opening the sample inserting opening; and
   means for exchanging the sample with a new one through said sample insertion opening when the sample rod is positioned in the second position.

2. The ultrasonic microscope according to claim 1, wherein said holding means includes a holder system attached to the lower end of the sample rod and a sample holder detachably supported by the holder system and to which the sample is attached.

3. The ultrasonic microscope according to claim 2, wherein said exchanging means includes an exchanging member for supporting the sample holder, inserting the sample holder, on which the sample has been held, into the gas-tight chamber through the sample inserting opening and attaching the sample holder to the holder system, when the sample inserting opening is opened.

4. The ultrasonic microscope according to claim 3, wherein said holder system and said sample holder include means for magnetically drawing them to each other.

5. The ultrasonic microscope according to claim 4, wherein said drawing means includes a coil attached to the holder system, means for supplying power to the coil to generate a magnetic field, and magnetizable material embedded in the sample holder and drawn to the holder system by a magnetic field thus generated.

6. The ultrasonic microscope according to claim 5, wherein said holder system includes magnetizable material and the magnetizable material in the same holder is a permanent magnet for drawing toward the magnetizable material in the holder system.

7. The ultrasonic microscope according to claim 6, wherein said means for supplying power to said coil includes means for supplying power to the coil selectively in one direction and in another direction reverse to said one direction to generate magnetic a field in different directions.

8. The ultrasonic microscope according to claim 3, wherein said sample holder has a screw hole in the side wall thereof and said sample inserting means has a rod provided at the front end thereof with a threaded portion which can be screwed into the screw hole in the side wall of the sample holder.

9. The ultrasonic microscope according to claim 1, wherein said exchanging means includes a rod which has a tip end for removably supporting the sample holder and is movable in a horizontal direction so that the tip end passes through the sample insertion opening with the sample holder supported by the tip portion.

10. The ultrasonic microscope according to claim 1, wherein said gas-tight chamber includes an upper portion having a diameter and a lower portion having a diameter larger than that of the upper portion, the sample insertion opening facing the lower portion so that the sample is exchanged in the lower portion.

* * * * *